United States Patent
Muehlig et al.

(10) Patent No.: US 7,137,734 B2
(45) Date of Patent: Nov. 21, 2006

(54) DEVICE FOR MEASURING QUANTITIES OF HEAT WHILE SIMULTANEOUSLY MEASURING THE EVAPORATION KINETICS AND/OR CONDENSATION KINETICS OF THE MOST MINUTE AMOUNTS OF LIQUID IN ORDER TO DETERMINE THERMODYNAMIC PARAMETERS

(75) Inventors: Peter Muehlig, Jena (DE); Thomas Klupsch, Jena (DE); Rolf Hilgenfeld, Luebeck (DE); Hans-Juergen Kiel, Wiegendorf (DE); Axel Walter, Jena (DE)

(73) Assignee: IMB Institut Fuer Molekulare Biotechnologie E.V., Jena (DE)

( * ) Notice: Subject to any disclaimer, the term of this patent is extended or adjusted under 35 U.S.C. 154(b) by 0 days.

(21) Appl. No.: 10/504,359

(22) PCT Filed: Feb. 11, 2003

(86) PCT No.: PCT/DE03/00432

§ 371 (c)(1),
(2), (4) Date: Aug. 12, 2004

(87) PCT Pub. No.: WO03/069292

PCT Pub. Date: Aug. 21, 2003

(65) Prior Publication Data

US 2005/0141587 A1 Jun. 30, 2005

(30) Foreign Application Priority Data

Feb. 12, 2002 (DE) ............................... 102 06 546

(51) Int. Cl.
*G01N 25/02* (2006.01)

(52) U.S. Cl. ............................. 374/27; 374/20; 374/31; 374/14

(58) Field of Classification Search .................. 374/14, 374/27, 34, 33, 17, 18, 19, 20, 28, 36, 38, 374/25; 73/61.77, 61.76, 64.56
See application file for complete search history.

(56) References Cited

U.S. PATENT DOCUMENTS 4,283,935 A * 8/1981 Eguchi et al. ................ 374/44
5,373,808 A * 12/1994 Sassa et al. ................. 117/216
5,470,154 A * 11/1995 Nishizawa et al. ......... 374/141

(Continued)

FOREIGN PATENT DOCUMENTS

DE 25 44 032 4/1977

(Continued)

*Primary Examiner*—Diego Gutierrez
*Assistant Examiner*—Mirellys Jagan
(74) *Attorney, Agent, or Firm*—Jordan and Hamburg LLP

(57) ABSTRACT

The invention relates to a device for measuring quantities of heat while simultaneously measuring the evaporation kinetics and/or condensation kinetics of the most minute amounts of liquid in order to determine thermodynamic parameters. The aim of the invention is to determine low thermal outputs, which are absorbed or released by the sample, as well as small differences between thermal outputs with regard to a reference measurement of the same magnitude. To this end, a most minute amount of liquid is located inside a measuring chamber having a constant temperature and air humidity. At least one thermal sensor is provided for repeatedly measuring the thermal radiation emitted from the most minute amount of liquid. A measuring means serves to determine the time-dependent change in the most minute amount of liquid. A computer is assigned to the measuring chamber in order to register, display, evaluate and/or subsequently process the measured values.

24 Claims, 3 Drawing Sheets

U.S. PATENT DOCUMENTS

Figure 1:
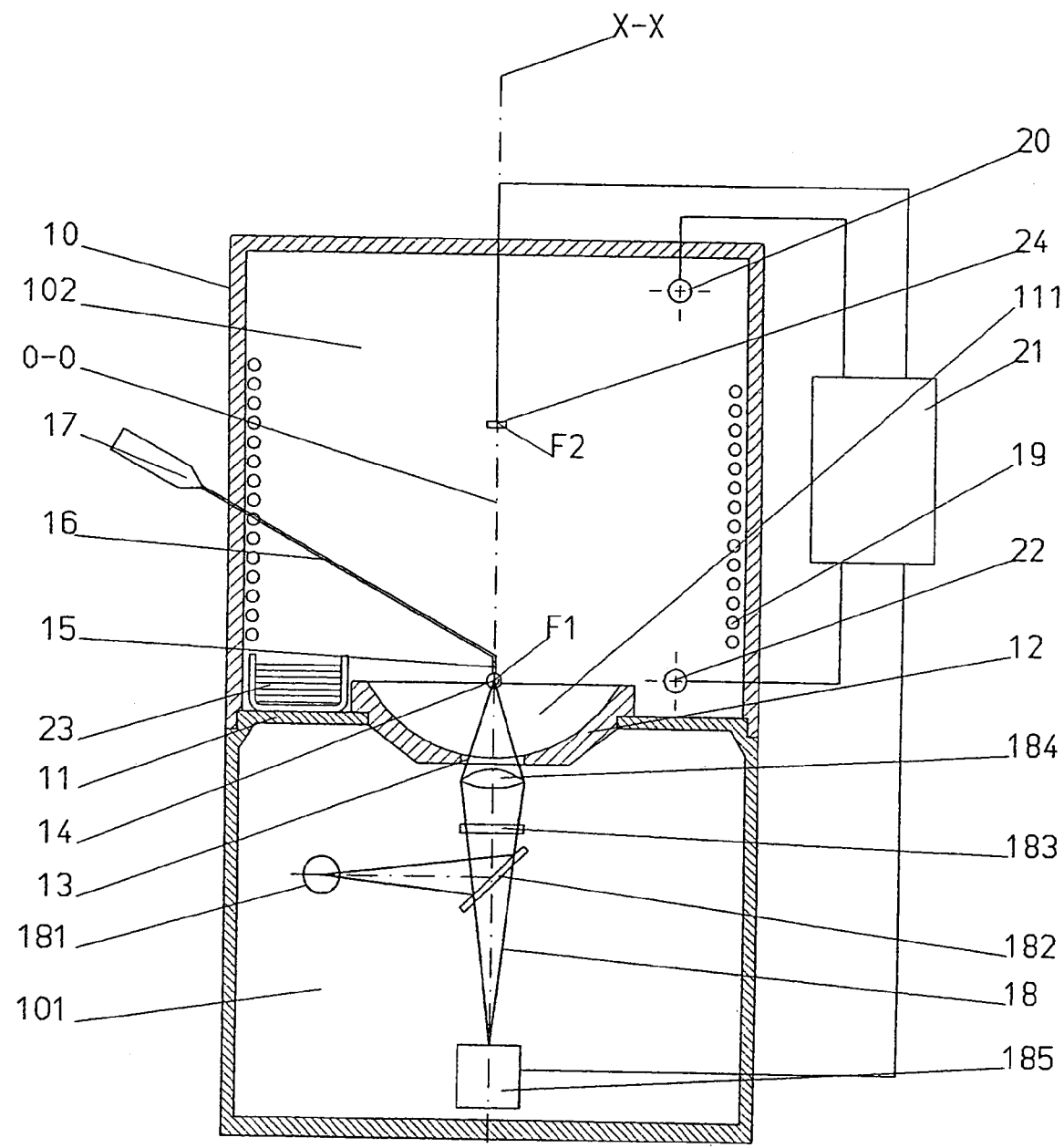

| | | | | |
|---|---|---|---|---|
| 5,758,968 A | * | 6/1998 | Diebold | 374/17 |
| 5,971,609 A | * | 10/1999 | Kijima et al. | 374/17 |
| 6,127,185 A | * | 10/2000 | Melton et al. | 436/60 |
| 6,443,616 B1 | * | 9/2002 | Brotz | 374/17 |
| 6,536,944 B1 | * | 3/2003 | Archibald et al. | 374/20 |
| 2002/0098592 A1 | * | 7/2002 | Neilson et al. | 436/147 |
| 2003/0041676 A1 | * | 3/2003 | Hajduk et al. | 73/862.041 |

FOREIGN PATENT DOCUMENTS

| | | |
|---|---|---|
| DE | 198 45 867 | 7/1999 |
| WO | WO 01 26797 | 4/2001 |

* cited by examiner

DEVICE FOR MEASURING QUANTITIES OF HEAT WHILE SIMULTANEOUSLY MEASURING THE EVAPORATION KINETICS AND/OR CONDENSATION KINETICS OF THE MOST MINUTE AMOUNTS OF LIQUID IN ORDER TO DETERMINE THERMODYNAMIC PARAMETERS

BACKGROUND OF THE INVENTION

This invention relates to a device for measuring quantities of heat while simultaneously measuring the evaporation kinetics and/or condensation kinetics of most minute amounts of liquid in order to determine thermodynamic parameters according to the species of patent claims. The quantities of heat can be absorbed during evaporation and/or released during condensation by very minute samples being mainly composed of liquid.

The inventive device predominantly serves to simultaneously measure the specific evaporation heat and vapor pressure of solutions at almost room temperature. Provided that a chemical equilibrium exists in the liquid and the evaporation process and/or condensation process are/is combined with a displacement of the chemical equilibrium, this device also serves to measure the specific chemical heat of reaction. For compound systems consisting of a solution being in contact with a solid (crystalline) phase of the solute, this device is used to measure the concentration of the saturated solution and the specific heat of solution, too. The most minute amount of liquid can also be a gel-like solvent-binding substance. The device is designated for measuring such kinds of solutions for which the vapor pressure of the solvent does not exceed the vapor pressure of the saturated water vapor in terms of magnitude and for which the vapor pressure of the solute above the solution has such a low value compared with the vapor pressure of the solvent that it can be ignored.

For all calorimeter principles to date the current state of art allows to derive the finding according to which the output that can still be measured becomes the smaller the faster the quantity of heat is released. The resulting characteristic time determines the minimum possible time constant required by the calorimeter to be able to measure the total quantity of heat released. Therefore, for maximum time constants of about 1000 s which are technically feasible today the output that can still be reliably measured is about 0.1 µW; it decreases down to about 10 nW for a time constant of 30 s. Consequently, the desired miniaturization of calorimeters for the application of very minute amounts of substances, e.g. when using thermally controlled micrometering cells based on chips, will only offer advantages for quantities of heat in the nJ range, if this quantity of heat is available within some seconds. This state-of-the-art finding is quite contrary to the demands placed on the measuring task to be solved by this inventive device.

SUMMARY OF THE INVENTION

Based on the state of the art, the aim of this invention is to determine small thermal outputs in the nW range which are absorbed or released during the evaporation and/or condensation of a portion of the liquid of the sample itself over a preferred period of time of 1000 s as well as to determine small differences of thermal outputs with regard to a reference measurement of the same magnitude. Since the thermal output to be measured also depends upon the speed of evaporation and/or condensation the aimed inventive device should also allow to measure the evaporation kinetics and/or condensation kinetics of most minute liquid samples, whereby these measurements shall also serve to simultaneously determine the vapor pressure of the liquid or small differences of the vapor pressure with regard to a reference sample. Due to the minute amounts of the samples it is necessary to perform the measurement in such a way that the influence of interferences on the measurement caused by the measuring process itself is., excluded as far as possible. Finally, it shall be possible to use the data directly gained during the measurement process (sample temperature, sample volume or sample mass over time) to compute back to the values of thermal output and vapor pressure, which are to be determined directly according to the procedure, by applying model analyses.

According to the invention this task is solved by the characteristic elements of the first patent claim and advantageously worked out by the elements of the subclaimes.

In one variant of the inventive device a sample will be located inside a measuring chamber where the temperature and vapor pressure of the solvent (relative air humidity or gas humidity) are kept at a constant level. The time-dependent spontaneous mass loss of the sample and spontaneous temperature decrease at the sample surface with regard to the temperature in the measuring chamber are measured simultaneously. Principally, the device is constructed in such a way that the sample is only in thermal contact with the gas in the measuring chamber and a substance transfer at the sample surface can only take place to the gas inside the measuring chamber. The surface temperature of the sample is measured in a pyrometric, i.e. a non-contact, manner. All the data are evaluated in a downstream computer aided peripheral system.

In the inventive device the sample itself represents the working substance of a calorimeter which is preferentially operated under the condition of the quasi-stationary heat exchange with the environment, whereby the thermal output released or absorbed by the sample is calculated from the variation in time of the temperature at the sample surface. The device is particularly designated to take measurements at minute samples, if the amount of heat to be registered is released very slowly. In this case, a dissolving power of the thermal output in the magnitude of 10 nW should be reached for a sample mass of about 1 mg at a time constant of 1000 s.

Based on the measuring values of the quantity of heat and vapor pressure directly to be measured, the inventive device is designated in particular to determine the derivable thermodynamic parameters such as the excess portion of the chemical potential or the enthalpy of the solvent which characterize the interaction between the solute and the solvent or between the molecules of the solvent. For compound systems, i.e. systems which contain solid and/or gel-like substances, this device is also used to directly determine parts of the phase diagram.

In particular, the performance parameters and constructive details of the inventive device are to fulfill the requirements which are to be placed on measurements of aqueous solutions of biological macromolecular compounds, such as proteins, with the inclusion of electrolyte and buffer additions. These requirements presume the following conditions:

a) Proteins, protein-monocrystals in particular, are often available in most minute quantities (in magnitudes of µg) only.

b) Protein solutions contaminate glass, silicon and other surfaces whereby these contaminations are difficult to be removed and require the application of chemically aggressive substances. These contaminations can make highly sensitive and expensive microchip-calorimeters unusable after a single measurement of protein solutions.

c) Compared with conventional (inorganic) systems the speed of growth or dissolving of protein crystals is lower by one to two magnitudes. This means that the thermal outputs to be measured for crystallization or dissolution are correspondingly lower.

d) Under normal conditions (room temperature, air pressure) the protein crystals are only stabile in permanent contact with the saturated solution and are moreover very sensitive to mechanic and thermal stresses. Therefore, the improper use of the protein crystals in calorimetric measurement procedures can lead to false results.

In addition to this, the inventive device is to allow to take thermodynamic measurements in a time-economic manner so that they can be used for the routine characterization (comparable with the differential thermal analysis for inorganic systems) in all studies of the crystal growth of proteins.

In the inventive device two independent measurements are performed simultaneously at the sample (aqueous solution) to be examined. In the whole course of measurement, first the mass loss of the sample will be registered as a result of the permanent evaporation of the solute due to the environmental conditions to be selected. Second, a calorimetric measurement of the evaporation heat per time unit is taken during the whole measurement process, whereby the working substance of the calorimeter arrangement, which represents the device, is the sample to be examined itself. This calorimetric measurement is performed in a non-invasive manner in such a way that the surface temperature of the sample is determined pyrometricly and permanently by means of at least one thermal sensor.

The sample to be examined (aqueous solution) is located in the inventive device inside a hermetically sealed measuring chamber in which the temperature and relative air humidity can be set exactly and kept at constant levels during the whole measurement procedure and temperature gradients and convection are almost avoided. The device is designed in such a way that the sample has only a thermal contact to its environment via its free interface with the surrounding gas room and a substance transfer of the sample to its environment can only happen via this free interface. To register the surface temperature of the sample in a pyrometric measurement, an elliptic concave mirror and a radiation receiver are located inside the measuring chamber. Their positions ensure that one focus of the concave mirror is exactly located on the interface of the sample to the measuring chamber and the other one is located on the sensor surface of the radiation receiver. Thus, this part of the free interface of the sample is imaged onto the aperture of the radiation receiver so that the surface temperature can be measured.

One variant of the device can be designed in such a way that the sample is provided as a hanging drop at the tip of a fine, vertically orientated capillary. The selected geometry of the capillary allows the hanging drop to develop with a possibly large diameter, referred to the outer diameter of the capillary, into coaxial direction towards the capillary (capillary with a wall thickness which is wedge-like reducing towards its tip, reached e.g. by grinding; outer or inner diameter at the tip of the capillary approximately 80 μm or 50 μm, respectively). Moreover, the surface of the capillary is passivated in its opening area (e.g. by applying a silane film) to avoid the deformation of the spherical drop shape or a mass loss of the drop due to the generation of a liquid film at the outer surface area of the capillary. In this case, the drop mass is determined by means of a measuring microscope inserted from the outside into the measuring chamber and being arranged in such a way that the drop is located in its object level and that it allows the measurement of the geometric parameters of the drop. In order to develop the drop the capillary can be shaped as a tip of a scale pipette that can be filled and operated from the outside. This pipette can simultaneously serve as a reservoir for the sample liquid and for the thermal equilibration of the sample before starting the measuring procedure.

A second possible construction of the device can have such a design that the sample to be examined is located in an upward opened, dish-shaped receptacle inside the measuring chamber. Thus, only the upper meniscus of the liquid is in contact with the volume of the measuring chamber. The receptacle must consist of an inert material which is very difficultly to be wetted and has an extremely low thermal conductivity. It must have the typical interior dimensions of a maximum diameter of 4 mm and a height of 1 mm. In this case, the sample mass is determined by weighing. For this purpose, the receptacle is connected to a scale of a high-accuracy scales with electromagnetic force compensation and a measuring accuracy of ca. 0.1 μg, whereby this scale is led into the measuring chamber. In this way, the mass of the liquid located in the receptacle can be permanently registered. To use this unit, a scale pipette projecting into the measuring chamber from the outside through the wall and being operated from the outside is fixed in such a way that it can be used for filling a defined amount of the sample liquid into the dish-shaped receptacle. At the same time, this scale pipette serves as a feeding reservoir and is used for the thermal equilibration of the liquid to be examined. For measurements of compound systems, consisting of a solution being in contact with a solid (crystalline) phase of the solute, this scale pipette can have such a large outlet that a small monocrystal (typical dimension of some hundreds μm) can be filled together with the liquid to be examined into the receptacle which is provided for receiving the solution. Finally, the wall of the measuring chamber can be provided with an opening for inserting a measuring microscope (e.g. an endoscope) which is arranged in such a way that the liquid meniscus in the dish-shaped receptacle and the monocrystal possibly contained in it can be observed.

According to this invention, the device comprises peripheral units for recording and evaluating data and for controlling purposes. The time-dependent registration of the geometric parameters of the hanging drop via the measuring microscope is preferentially performed through a downstream image processing system.

The vapor pressure of the solution (e.g. water) in the measuring chamber is determined at a great distance to the sample via the relative humidity inside the measuring chamber. Normally, it is lower than the equilibration vapor pressure of the solvent above the solution, which directly exists above the liquid meniscus. The sample is supplied into the measuring chamber as soon as the temperature of the sample liquid located in the pipette has adapted to the temperature existing inside the measuring chamber (temperature differences of up to 1° C. are permissible). Due to the directed diffusion from the free interface of the sample to the volume of the measuring chamber, the evaporation of the solvent directly starts after the supply of the sample. The evaporation rate of the solvent is determined from the measured time-dependent change of the mass of the sample. It is the base for calculating the equilibration vapor pressure of the solvent.

The evaporation of the solvent causes a temperature decrease of the sample referred to the temperature in the measuring chamber (at a great distance to the drop). This process continues up to the point at which the evaporation heat to be temporally applied (evaporation enthalpy of the solvent) and the thermal output lead to the drop by heat transfer from the gas room of the measuring chamber have almost balanced out and a quasi-stationary temperature difference is reached. The determination of the evaporation enthalpy of the solvent is based both on the pyrometricly measured time-dependent difference of the temperatures at the sample surface on one side and in the measuring chamber on the other side and on the involved measured time-dependent evaporation rate of the sample.

The continuous evaporation of the solvent during the measuring process results in a permanently increasing concentration of the solution and therefore in a permanent change (generally a reduction) of the vapor pressure of the solvent as long as the dissolved components do not crystallize. In particular, characteristic deviations of the evaporation rate arise compared to a sample consisting of a pure solvent. These deviations are measured and serve as the base for calculating the excess portion of the chemical potential of the solvent as the target value. As a result of the increasing concentration of the solution during the measurement procedure, the evaporation enthalpy of the solvent also depends on the time. From the characteristic deviations, referred to the constant evaporation enthalpy of the pure solvent, the excess portion of the molecular enthalpy of the solvent in the solution is calculated as the target value.

If the relative air humidity in the measuring chamber is set to such a value that the vapor pressure of the solvent in the measuring chamber is lower than the one above the saturated solution, an initially undersaturated solution exhibits a temporary increase of the concentration exceeding the saturation concentration as a result of the delayed nucleation kinetics if the crystalline phase. If a small monocrystal of the typical dimensions above mentioned is put into the undersaturated solution of a well-known concentration at a suitable moment of time, its dimensions will initially decrease due to dissolution up to the point of transition into the range of a supersaturated solution in which the crystal grows. In this process, the mass of the delivered crystal has such a low value that the additional increase in the concentration of the solution due to the dissolution of the crystal can be ignored. By means of the measuring microscope and a possibly downstream image processing system the time-dependent dimensions of the delivered crystal are registered and the saturation concentration (point in the phase diagram) is determined via the point in time at which the transition from dissolution to growth happens.

For delivered monocrystals having sufficiently large dimensions (possibly larger than the ones indicated above) the transition from dissolution to growth is registered in the pyrometric temperature measurement as a significant salient point, because a change from consumed solution heat to released solution heat takes place. As far as observations by means of the measuring microscope allow to determine the dissolution rate or growth rate (mass per time) of the crystal, the molecular solution enthalpy can be calculated from the data gained by the pyrometric temperature measurement. These rates in turn are the base for calculating the temperature dependence of the saturation concentration (curve in the phase diagram).

For all variants of the inventive design it is possibly required to perform calibration measurements of solutions with a well-known vapor pressure or evaporation heat. When doing this for measurements of the hanging drop, such errors of measurements are eliminated which are due to the fact that the signal at the radiation receiver additionally shows a weak dependence upon the drop radius. If the sample is put into the dish-like receptacle, the calibration measurements will be used to determine the transition coefficients of the heat and substance transfers between the sample and the measuring chamber.

All variants of the inventive device can be expanded in such a way that several most minute amounts of liquid are arranged in the same manner inside a common measuring chamber so that the surface temperature and the evaporation kinetics or condensation kinetics can be measured for all most minute amounts of liquid simultaneously. If these most minute amounts of liquid include a sample with a well-known evaporation heat and vapor pressure, the measuring data of the other samples can be referred to this known sample in order to eliminate such errors of measurement which are due to the imprecise determination of temperature and vapor pressure in the measuring chamber at a great distance to the most minute amounts of liquid.

Unlike conventional calorimeters the inventive device uses the measured time-dependent temperature difference $\Delta T(t)$ of the working substance to the environment as a measure for the thermal output $N(t)$ released or absorbed by the sample as long as quasi-stationary conditions are maintained, i.e. that $N(t)$ shows such a slow time-dependent change that the curve of $N(t)$ at earlier points of time than the time of measurement t turns out to be only a little correction to $\Delta T(t)$. The typical thermal outputs to be measured in practical operation by means of this device according to its type of design and intended use range between 10 and 100 µW and change with a characteristic time constant $\tau = |N(t)/(dN(t)/dt)| \geq 1 \cdot 10^3$ s. Theory shows that quasi-stationary conditions exist for this. Then, for measurements performed at the hanging drop a sensibility of $\Delta T(t)/N(t) \cong 1/(4\pi\alpha_g R_0(t))$ follows, whereby $R_0(t)$ is the time-dependent drop radius and $\alpha_g$ is the heat conductivity of air. The result is $\Delta T(t)/N(t) \cong 6 \cdot 10^3$ K/W for the typical values of $R_0 = 5 \cdot 10^{-4}$ m and $\alpha_g = 0.025$ W/K·m.

The theoretic dissolving power of the arranged device for the measurement of $N(t)$ is limited by two principal influencing factors: the noise of the thermal sensor in connection with the downstream electronic system and the accuracy of the determination of the evaporation rate. For the pyrometric temperature measurement a high-sensitive thermal sensor is used. It has a maximum spectral sensitivity in the spectral range of the maximum value of the radiation of the black body at room temperature, i.e. in the spectral range of about 10 µm or above. This ensures that the measurement of the surface temperature of the hanging drop is almost independent on the special composition of the aqueous solution. For this purpose, a commercial thermal sensor which does not require cooling is suitable. Its time constant is about 60 ms. The dynamic range of this thermal sensor is $\geq 10^5$. This allows a comfortable calibration of the thermal sensor to the temperature to be measured in the upper range of the registered radiation output.

The detection sensitivity of the thermal sensor has been determined as 170 µV/K in practical operation by using a device working with a hanging drop. Considering the influence of the peripheral electronics, in the pyrometric measurement a noise-related error of measurement of the registered voltage values of ±0.5 µV exists for an optimum scanning sequence frequency of 10 Hz. This value corresponds to an error of temperature measurement of $\pm 3 \cdot 10^{-3}$ K per single measurement. In the subsequent computer-aided evaluation, the temperature data over characteristic time intervals of a period of $\tau$ are adapted to the ideal theoretic curve. When doing this, the statistic error $(\delta T)_{stat}$ of the temperature measurement to be supposed reduces down to $(\delta T)^{stat} = \pm 3 \cdot 10^{-5}$ K, corresponding to a theoretic noise-related contribution to the resolution limit of the output of $(\delta N)_R \cong 5 \cdot 10^{-9}$ W registered by the device.

The theoretic accuracy limit with which the sample mass of the hanging drop can be determined is given by the measuring uncertainty $\delta R_0$ for determining the drop radius, i.e. by the limit of the microscopic resolution. For an observation microscope having an aperture of <1 an aperture-related error of measurement of $\delta R_0 \approx 5 \cdot 10^{-7}$ m exists for a single measurement. When performing an automated measurement by image analysis it is possible to measure the drop radius every 10 s. In the subsequent computer-aided evaluation the data of the drop radius over characteristic time intervals of a period $\tau$ are adapted to the ideal theoretic curve. When doing this, the statistic error of the radius measurement reduces down to $(\delta R_0)_{stat} = \pm 5 \cdot 10^{-8}$ m. Based on this value, an additional error $(\delta N)_{Ap}$ results for the measurement of the thermal output. It follows from $(\delta N)^{Ap}/N(t) \approx 3 \cdot (\delta R_0)_{stat}/R_0(t) \approx \pm 3 \cdot 10^{-4}$ and is proportional to the measured output $N(t)$. $(\delta N)_{Ap}$ has the magnitude of the theoretic noise-related resolution limit $(\delta N)_R$, if outputs in the order of 10 µW are measured.

For a device, which is equipped with a dish-like receptacle for the sample, higher values (but of the same magnitude as the ones of the hanging drop) can be reached principally for the sensitivity, the time constant and the noise-related resolution limit of the output measurement, because due to the reduced free surface the transition coefficients of the heat and solvent transfers between the sample and the measuring chamber are smaller than the ones for the hanging drop. For the determination of the evaporation rate of the sample of time-dependent sample masses $m(t)$ of 5 mg, weighing operations with an accuracy of $\pm 0.1$ µg can be performed at time intervals of 1 s when using high-accuracy scales and when considering the performance capacity of the downstream A/D converters. In the subsequent computer-aided evaluation, these data are adapted to the ideal theoretic curve over characteristic time intervals of a period of $\tau$. When doing this, the statistic error of the weighing is improved down to $(\delta m)_{stat} = \pm 3 \cdot 10^{-9}$ g. Thus, an error $(\delta N)_W$ is caused for the determination of $N(t)$ according to $(\delta N)_W/N(t) \approx (\delta m)_{stat}/m(t) \approx \pm 1 \cdot 10^{-6}$. For $N(t)$ in the order of 10 µW, $(\delta N)_W$ has the magnitude of $10^{-11}$ W and therefore it is smaller than the noise-related resolution limit.

DETAILED DESCRIPTION OF THE INVENTION

Figure 2:
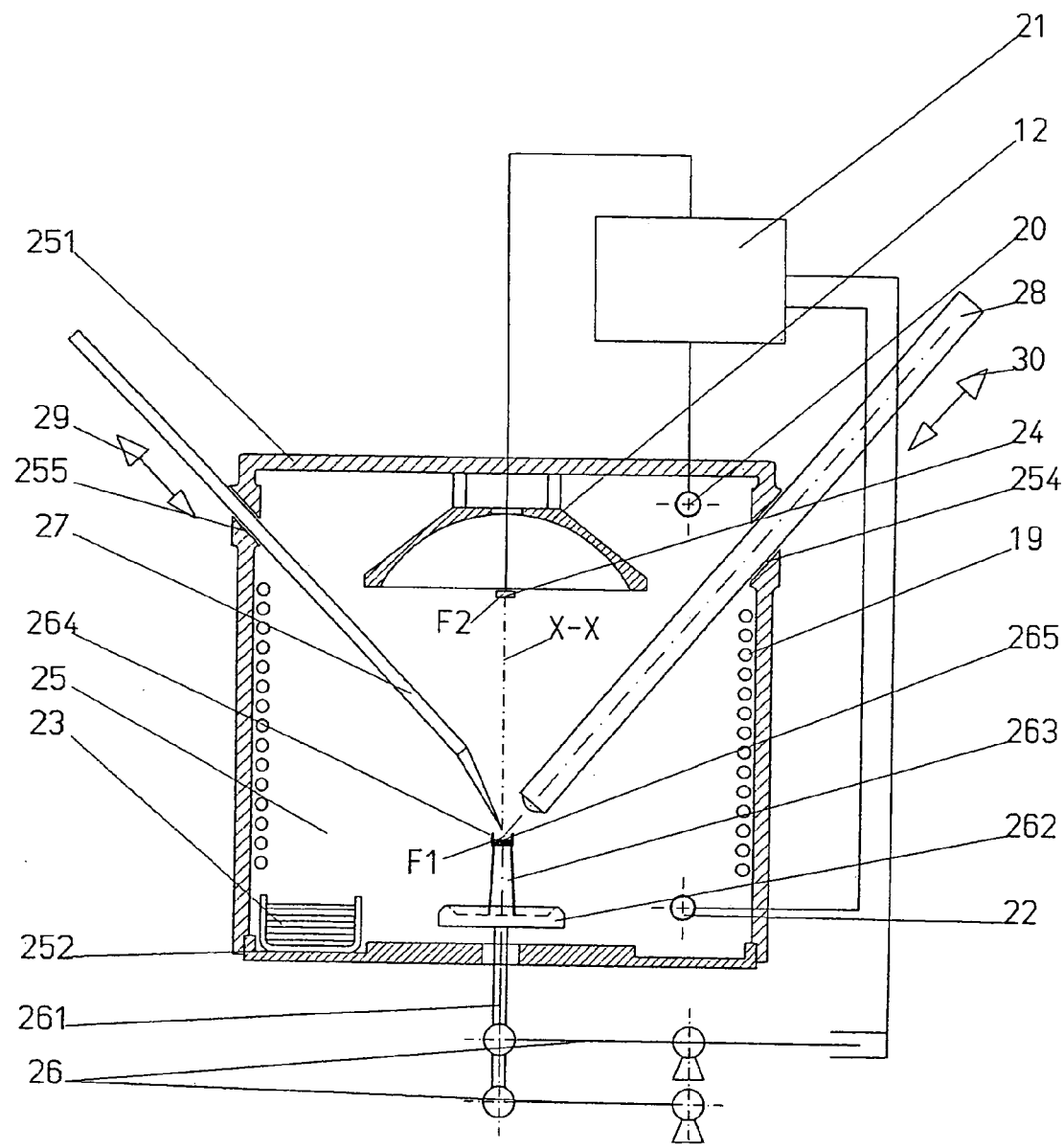
Figure 3:
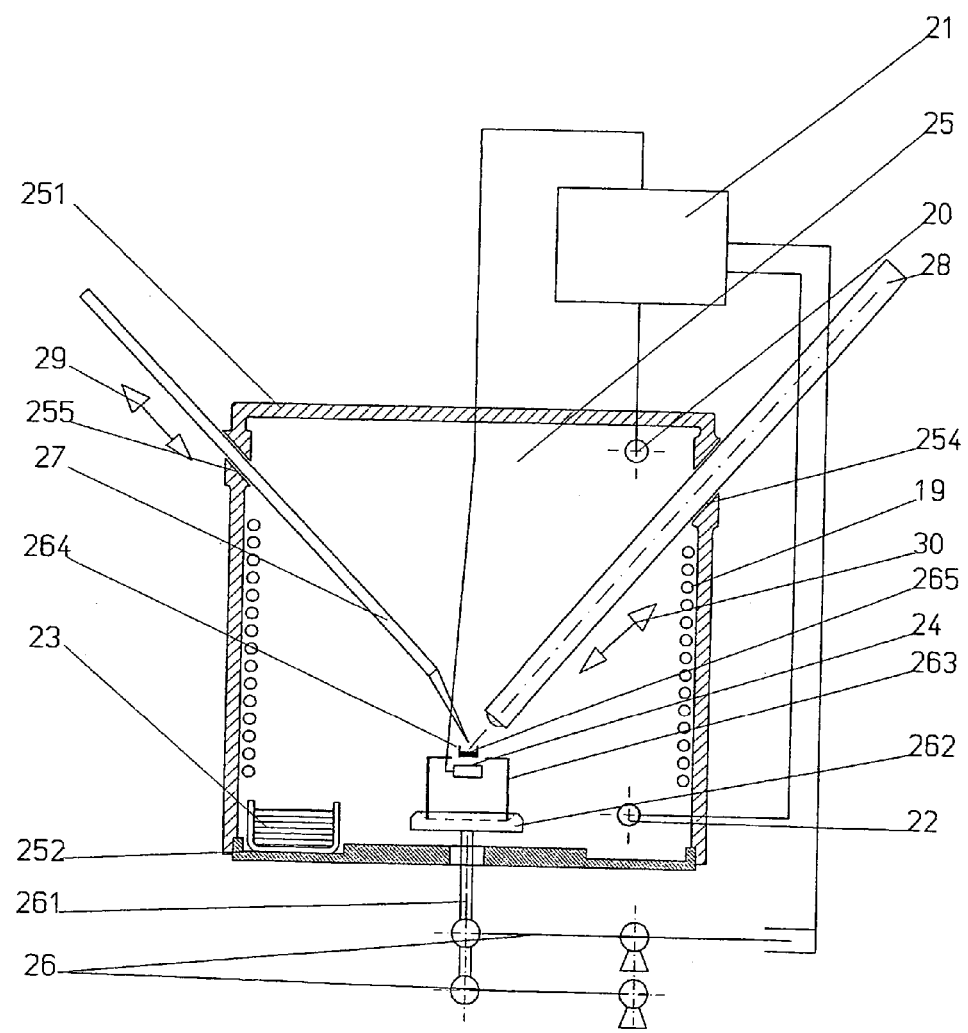

In the following, the invention is explained in more detail by means of the schematic drawing with upright projections of three design variants of the device. The figures show:

FIG. 1 a first inventive device in which the sample is provided as a hanging drop, FIG. 2 a second inventive device in which the sample liquid is located in a dish-like receptacle, and FIG. 3 a third inventive device with the direct measurement of the heat radiation.

In FIG. 1 a gas-tight measuring chamber 10 with a geometric axis X—X is divided into two parts 101 and 102 by carrying elements 11, whereby the upper part 102 can be placed onto the lower part 101 after having completed the preparations which are required for the measurement. The carrying elements 11, which are designed as struts or as an intermediate bottom and are provided with a central opening 111, are to carry an elliptic mirror 12 which fills out the central opening 111 or is at least located in it and has an optic axis O—O that preferentially coincides with the geometric axis X—X. The elliptic mirror 12 allows the transmission of radiation in its central part 13 and has two focuses $F_1$ and $F_2$ on its optical axis O—O, whereby a liquid drop 14 of a solution is located in focus $F_1$ (and in its direct environment and therefore: focal spot) and a thermal sensor 24 is located in focus $F_2$ (and in its direct environment=focal spot). The diameter of the drop 14 shall be <2 mm and the amount of sample liquid contained in it shall be <4 µl. The drop 14 is hanging freely and under the effect of gravity perpendicularly at a capillary 15 which has a diameter of <300 µm and is connected to a micropipette 17 via a (flexible) pipe or hose 16. A working beam path 18 is used for the simultaneous determination of the diameter of the drop. This path is mainly positioned in the measuring chamber part 101 and contains a light source 181, a beam splitter 182, a filter 183 and an objective 184 as well as an optic sensor 185 (e.g. a CCD camera) as optical elements. The drop 14 is illuminated by the light source 181 via the beam splitter 182 and the objective 184. The working beam path 18 being reflected and scattered at the drop 14 reaches the optic sensor 185 via the objective 184 and the beam splitter 182 and generates an image of the drop there. The optical filter 183 arranged in the working beam path 18 removes all perturbing radiation which could have an influence on the thermal equilibration of the drop 14 and its environment. A cooling/heating system 19 is used to maintain or control the temperature inside the measuring chamber 10. It is controlled by a computer 21 via a temperature sensor 20. To maintain a constant humidity inside the measuring chamber 10, a humidity sensor 22 and a humidity dispenser or dryer 23 are provided and also controlled by the computer 21. Finally, the data measured of the surface temperature are received by the thermal sensor 24 and the data of the time-dependent change of the drop diameter are received by the sensor 185. They are saved and evaluated in the computer 21.

The following example of measurement uses water as solvent and at the start of measurement it contains 20 mM HCl+50 mM Na Citrat+1% Phenol (pH=6.5) dissolved as electrolytic and buffer components as well as 0.6 mg/ml dissolved protein having a molecular weight of 35000 (special insulin mutants). For this measurement a measurement is performed at a reference system having the same components but not including protein. This reference measurement simplifies the task which is to determine the contributions to those measured data which are directly caused by the protein proportion of the solution. To achieve defined conditions, all measurements will be finished in this example as soon as the drop volume has reached half of the start value or the concentration of the dissolved substances has double the volume of the start value. For this example, the actual measurement needs 1620 s and the reference measurement needs 2900 s.

|  | Measurement Start value | Measurement End value | Reference measurement Start value | Reference measurement End value |
|---|---|---|---|---|
| Temperature in the measuring cell in ° C. | 23.4 | 23.4 | 23.4 | 23.4 |
| Relative air humidity in the measuring cell in % | 72.4 | 72.4 | 72. | 72.6 |
| Drop radius in mm | 0.742 | 0.589 | 0.753 | 0.597 |
| Time-dependent change of the drop radius in μm/s | −72 | −104 | −55 | −55 |
| Drop temperature decrease in K | 5.78 | 6.25 | 3.28 | 3.24 |
| Absorbed thermal output in mW | 1.34 | 1.15 | 0.776 | 0.607 |
| Vapor pressure of the solvent in kPa | 2.48 | 1.94 | 2.4 | 2.35 |

Due to evaporation the drop radius decreases and the concentration of the dissolved components increases in the course of measurement. Therefore, it can be seen that the start data of the drop radius, the drop temperature, the absorbed thermal output and the vapor or gas pressure of the solvent contained in the table above change more or less significantly. Interesting thermodynamic data which are defined by the protein proportion can be determined on the basis of the temporal curve of the measured data compared to the reference system. The example above results in $\mu_2^{(ex)}/kT=0.38$, $\mu_3^{(ex)}/kT=-0.14$, $h_2^{(ex)}/kT=8.86$, $h_3^{(ex)}/kT=-4.08$, with $\mu_2^{(ex)}$, $\mu_3^{(ex)}$ being the (molecular) chemical excess potentials of the solvent of second and third orders in the solution (referred to the total concentration dependency), $h_2^{(ex)}$, $h_3^{(ex)}$ being the molecular excess enthalpies of the solvent of second and third orders in the solution (referred to the total concentration dependency), k being the Boltzmann's constant and T being the absolute temperature.

In this example of measurement both the measured data given in the table and the corresponding differences to the reference measurements are considerably higher than the noise-related errors of measurement derived above. However, the smallness of the noise-related errors of measurement will be for example of high importance, if under the conditions of a very slow drop kinetics (time-dependent changes of the drop radius <10 μm/s) low differences (in the range of 1%) to the corresponding reference measurements are to be determined reliably.

FIG. 2 shows a measuring chamber 25, the upper part 251 of which is formed by a hollow body, preferentially a hollow cylinder, can be hermetically closed by a bottom 252. A rod-shaped holder 261 of a scale 262 of an ultra-microbalance (high-accuracy scales) 26 is led through the bottom 252. A small dish or bowl 264 having a capacity of P10 μl and containing the sample liquid 265 is located directly or via a holder 263 on this scale 262, whereby this small dish 264 is thermally isolated from its support. To deliver the sample liquid a manipulator 27 is used which projects into the measuring chamber 25 through an opening 255 in the wall of the upper part 251 and is adjustable in its perpendicular direction as indicated by the double-arrow 29. The ultra-microbalance 26 is used to determine the sample mass; according to the compensation principle it keeps the vertical position of the meniscus of the liquid 265 constant due to its rigid coupling to the scale 262 via the holder 263. The sample liquid 265 is in the focus (focal spot) F1 or its environment of an elliptic mirror 12 which is attached to the top of the upper part 251 and a thermal sensor 24 is in the other focus (focal spot) F2 or its direct environment of this mirror 12. The great axis of the ellipse of the mirror 12, on which the focuses F1 and F2 are located, coincides with the geometric axis X—X of the measuring chamber 25. To stabilize or control the environmental temperature (∩T P 0,1° C.) and air humidity (∩rF P 0,1%) a temperature sensor 20 with a heating/cooling system 19 and a humidity sensor 22 with a humidity dispenser/dryer system 23 are located in the measuring chamber 25. The two systems as well as the ultra-microbalance 26 are connected to a computer 21 which saves the measured data of the heating/cooling system 19 and of the hymidity dispenser/dryer system 23 and controls the two systems. A measuring microscope 28 projecting into the measuring chamber 25 through an opening 254 can be adjusted towards the double arrow 30 and serves to observe the sample liquid 265. For example, it is possible to observe the changes of a crystal led into the sample liquid 265 by means of the manipulator 27 and the changes of the dissolved substance by using a measuring microscope 28 which can be an endoscope in the example given.

The device shown in FIG. 2 can also be used to measure the time-dependent changes of the volume of the sample and of the temperature. Based on these data the vapor pressure and the specific evaporation heat of the solvent of the substance as well further thermodynamic parameters can be determined by the software installed in the computer 21.

Like in FIG. 2, in FIG. 3 a measuring chamber 25 consists of a hollow cylinder 251 and a bottom 252. The bottom is provided with a central opening 253 and carries eccentrically a humidity dispenser or dryer 23. The rod-shaped holder 261 of a scale 262 being part of an ultra-microbalance 26 is led through the opening 253. On the scale 262 a holder 263 of a small dish 264 including the sample liquid 265 is positioned. The small dish 264 exhibits the properties of a grey IR radiator. The hollow cylinder 251 is provided with two openings 254 and 255 for inserting an endoscope 28 and a manipulator 27; both can be moved in these openings 254, 255 towards the double arrows 30 or 29, respectively. Moreover, a cooling and heating system 19 in form of a spiral fixed at the side walls of the cylinder, a temperature sensor 20, a humidity sensor 22 and a thermal sensor 24 are located inside the hollow cylinder 251. They are used for control and regulation purposes and are connected to a computer 21. Considering the maximum ratio of aperture of the thermal sensor 24, it is installed at a possibly small distance to the holder 263, in this case ca. 1 mm below the holder 263, and it is thermally isolated and decoupled. Thanks to the compensation principle of the ultra-microbalance 26 the distance between the thermal sensor 24 and the small dish 264 will remain constant, if the mass of the sample liquid 265 changes. To keep the temperature in the measuring chamber at a constant level or to regulate it, the cooling and heating system 19 is controlled by the computer 21 according to the temperature absorption of the sensor 20. The humidity dispenser or dryer 23 is controlled by the computer 21 according to the measured values transferred by the sensor 22 to the computer 21 in order to maintain a constant gas humidity inside the measuring chamber 25. The registered data of the thermal sensor 24 and the scales 26 are also transferred to the computer 21 where they are processed to gain, set or indicate the quantities of heat, the vapor pressure, the evaporation kinetics or the thermodynamic parameters.

For a measurement of a solution the start composition of which follows the measurement example to FIG. 1, 8 mg of a liquid are filled into the flat dish-shaped receptacle 264 at a measuring chamber temperature of 26.8° C. and a relative air humidity of 65.0%, and the initial changes in mass of −1.75 μg/s and an initial temperature decrease of the sample of 1.35° C. are registered. These data correspond to an initial power consumption of the sample of 3.9 μW. Compared to the reference system the initial differences in the decrease in mass are about 0.1 μg/s and in the decrease of sample temperature about 0.3° C. These values correspond to a difference in the power consumption of 860 nW. The further process is continued analogue to the measurement example to FIG. 1 mentioned above.

All the elements demonstrated in the description, the subsequent claims and the drawing can be essential for this invention both individually and in any combination.

List of reference numerals

| | |
|---|---|
| 10, 25 | measuring chambers |
| 11 | carrying elements |
| 12 | elliptic mirror |
| 13 | central part |
| 14 | liquid drop |
| 15 | capillary |
| 16 | pipe or hose connection |
| 17 | micropipette |
| 18 | working beam path |
| 19 | cooling/heating system |
| 20 | temperature sensor |
| 21 | computer |
| 22 | humidity sensor |
| 23 | humidity dispenser or dryer |
| 24 | thermal sensor |
| 26 | ultra-microbalance, high-accuracy scales |
| 27 | manipulator |
| 28 | measuring microscope |
| 29, 30 | double arrows |
| 101, 252 | lower part, bottom |
| 102, 251 | upper part, hollow cylinder |
| 111 | central opening |
| 181 | light source |
| 182 | beam splitter |
| 183 | filter |
| 184 | objective |
| 185 | optic sensor |
| 253 | central opening |
| 254, 255 | openings |
| 261 | rod-shaped holder |
| 262 | scale |
| 263 | holder |
| 264 | small dish, bowl |
| 265 | sample liquid |
| X—X | geometric axis |
| Y—Y | optic axis |
| $F_1, F_2$ | focuses |

The invention claimed is:

1. An apparatus for measuring quantities of heat while simultaneously measuring evaporation kinetics and/or condensation kinetics of a predetermined amount of liquid containing a uniform evaporating and/or condensing component for determining thermodynamic parameters, comprising:

a measuring chamber;

means for receiving a predetermined amount of the liquid in the measuring chamber;

means for maintaining a constant temperature and a constant vapor pressure of the liquid in the measuring chamber;

at least one thermal sensor for repeatedly measuring thermal radiation emitted by the amount of liquid;

measuring means for determining time-dependent change in the concentration and phase of the predetermined amount of liquid; and a computer, communicating with the thermal sensor and the measuring means, the computer registering, displaying, evaluating and/or subsequently processing data measured by the measuring means and thereby measuring quantities of heat while simultaneously measuring evaporation kinetics and/or condensation kinetics of the predetermined amount of liquid.

2. The apparatus of claim 1, wherein the measuring chamber is closed gastight.

3. The apparatus of claim 1, wherein the thermal sensor is positioned to be close to the liquid.

4. The apparatus of claim 1, further comprising a measuring microscope for observing and/or measuring the liquid including any solid phase contained in it, the measuring microscope penetrating the wall of the measuring chamber and being arranged in such a way that it can be adjusted.

5. The apparatus of claim 1, further comprising a heating/cooling coil fixed along a side wall of the measuring chamber for heating or cooling the measuring chamber.

6. The apparatus of claim 1, further comprising a humidifier and/or dryer located in the measuring chamber.

7. The apparatus of claim 1, further comprising means for generating a constant vapor pressure in the liquid.

8. The apparatus of claim 1, further comprising means for regulating atmosphere of the measuring chamber by heating, cooling, humidifying and/or drying said atmosphere, and wherein said computer further comprises means for controlling die regulating means.

9. The apparatus of claim 1, wherein the means for receiving the liquid is adapted to receive a plurality of the predetermined amount of liquid.

10. The apparatus of claim 1, further comprising an elliptic reflector arranged in the measuring chamber, the elliptic reflector having two focal points, the liquid being located at one of said focal points and the thermal sensor being located at the other of said focal points.

11. The apparatus of claim 10, further comprising a receptacle for the liquid and wherein said one focal point is on a free interface of the liquid and said other focal point is on a surface of the thermal sensor.

12. The apparatus of claim 1, further comprising a receptacle for the liquid.

13. The apparatus of claim 12, wherein the measuring means for determining time-dependent change in the liquid comprises a high-accuracy scale for receiving the liquid and determining time-dependent change in mass of the very liquid.

14. The apparatus of 13, wherein the scale is located inside the measuring chamber.

15. The apparatus of claim 1, wherein the measuring chamber is for holding the liquid in form of a hanging drop.

16. The apparatus of claim 15, further comprising a measuring pipette and an adjustable capillary projecting into the measuring chamber for forming the drop.

17. The apparatus of claim 15, wherein the measuring means for determining time-dependent change in the liquid comprises optic measuring means for determining time-dependent change in the geometry of the drop.

18. The apparatus of claim 17, further comprising a filter for the optic measuring means to block disturbing radiation.

19. A method for measuring quantities of heat while simultaneously measuring the evaporation kinetics and/or condensation kinetics of a predetermined amount of liquid containing a uniform evaporating and/or condensing component for determining thermodynamic parameters, comprising:

providing a predetermined amount of liquid inside a measuring chamber;

maintaining a constant temperature and a constant vapor pressure of the liquid by at least one thermal sensor repeatedly measuring thermal radiation emitted by the liquid;

measuring and thereby determining time-dependent change in the concentration and phase of the predetermined amount of liquid; and registering, displaying, evaluating and/or subsequently processing the measured data by means of a computer and thereby measuring quantities of heat while simultaneously measuring evaporation kinetics and/or condensation kinetics of the predetermined amount of liquid.

20. The method of claim 19, wherein the liquid is located in the measuring chamber in form of a hanging drop.

21. The method of claim 19, wherein the liquid is a solution.

22. The method of claim 19, wherein the liquid contains a solid phase of a dissolved substance.

23. The method of claim 19, wherein the liquid contains a gel-like solvent-binding substance.

24. The method of claim 19, comprising providing a plurality of the predetermined amount liquid in the measuring chamber.

* * * * *